US011617779B2

(12) United States Patent
Sullenger et al.

(10) Patent No.: US 11,617,779 B2
(45) Date of Patent: Apr. 4, 2023

(54) INHIBITION OF ENDOSOMAL TOLL-LIKE RECEPTOR ACTIVATION

(71) Applicant: DUKE UNIVERSITY, Durham, NC (US)

(72) Inventors: Bruce A. Sullenger, Durham, NC (US); Jaewoo Lee, Durham, NC (US)

(73) Assignee: Duke University, Durham, NC (US)

( * ) Notice: Subject to any disclaimer, the term of this patent is extended or adjusted under 35 U.S.C. 154(b) by 543 days.

(21) Appl. No.: 15/291,849

(22) Filed: Oct. 12, 2016

(65) Prior Publication Data

US 2017/0095503 A1 Apr. 6, 2017

Related U.S. Application Data

(62) Division of application No. 13/496,313, filed as application No. PCT/US2010/002516 on Sep. 16, 2010, now Pat. No. 9,468,650.

(60) Provisional application No. 61/243,090, filed on Sep. 16, 2009.

(51) Int. Cl.

| A61K 38/16 | (2006.01) |
| A61K 38/17 | (2006.01) |
| A61K 31/70 | (2006.01) |
| A61K 31/13 | (2006.01) |
| A61K 31/722 | (2006.01) |
| A61K 31/785 | (2006.01) |

(52) U.S. Cl.
CPC .............. *A61K 38/16* (2013.01); *A61K 31/13* (2013.01); *A61K 31/70* (2013.01); *A61K 31/722* (2013.01); *A61K 31/785* (2013.01); *A61K 38/1709* (2013.01)

(58) Field of Classification Search
None
See application file for complete search history.

(56) References Cited

U.S. PATENT DOCUMENTS

| 7,300,922 B2 | 11/2007 | Sullenger et al. |
| 7,304,041 B2 | 12/2007 | Rusconi |
| 7,611,835 B2 | 11/2009 | Kim et al. |
| RE43,612 E | 8/2012 | Anderson et al. |
| 2003/0083294 A1 | 5/2003 | Sullenger et al. |
| 2003/0143217 A1 | 7/2003 | Baird et al. |
| 2003/0180250 A1 | 9/2003 | Chauhan et al. |
| 2006/0040881 A1 | 2/2006 | Rusconi |
| 2008/0199485 A1 | 8/2008 | Kundig et al. |
| 2008/0267903 A1 | 10/2008 | Uchegbu et al. |
| 2009/0048193 A1 | 2/2009 | Rusconi et al. |
| 2009/0082250 A1 | 3/2009 | Hart et al. |
| 2009/0208501 A1 | 8/2009 | Visintin et al. |
| 2009/0298710 A1 | 12/2009 | Farokhzad et al. |
| 2010/0210746 A1 | 8/2010 | Gustafson et al. |
| 2010/0249217 A1 | 9/2010 | Sullenger et al. |
| 2010/0285081 A1 | 11/2010 | Chen et al. |
| 2011/0118187 A1 | 5/2011 | Sullenger et al. |
| 2012/0128782 A1 | 5/2012 | Green et al. |
| 2012/0183564 A1 | 7/2012 | Sullenger |
| 2013/0266664 A1 | 10/2013 | Yang et al. |

FOREIGN PATENT DOCUMENTS

| WO | WO 2002/019822 | 3/2002 |
| WO | WO 2002/053185 | 7/2002 |
| WO | WO 2003/002592 | 1/2003 |
| WO | WO 2006/040579 | 4/2006 |
| WO | WO 2008/000517 | 1/2008 |
| WO | WO 2008/063157 | 5/2008 |
| WO | WO 2008/121354 | 10/2008 |
| WO | WO 2010/020008 | 2/2010 |
| WO | WO 2013/040552 | 3/2013 |

OTHER PUBLICATIONS

Bompiani et al. "Probing the Coagulation Pathway with Aptamers Identifies Combinations that Synergistically Inhibit Blood Clot Formation" (2014) Chemistry & Biology 21: 935-944.

Chase, et al., "Single-stranded DNA binding proteins required for DNA replication," (1986) Ann. Rev. Biochem. 55:103-136.

Eichhorn, G.L. et al., "Interaction of metal ions with polynucleotides and related compounds. XII. The relative effect of various metal ions on DNA helicity," (1968) Journal of the American Chemical Society 90(26):7323-7328.

Holl, et al., "Nucleic acid scavenging polymers inhibit extracellular DNA-mediated innate immune activation without inhibiting antiviral responses," (2013) Plos One, 8(7):1-10.

Holl et al., "The nucleic acid scavenger polyamidoamine third-generation dendrimer inhibits fibroblast activation and granulation tissue contraction" (2014) Plast Reconstr Surg 134: 420e-33e.

Joachimi, A. et al., "A new anticoagulant-antidote pair: Control of thrombin activity by aptamers and porphyrins," (2007) Journal of the American Chemical Society 129(11):3036-3037.

Lee et al., "Nucleic acid-binding polymers as anti-inflammatory agents," (2011) Proc. Natl. Acd. Sci. 108(34):14055-60.

Lichner, Z. et al., "Double-stranded RNA-binding proteins could suppress RNA interference-mediated antiviral defences," (2003) J. Gen. Virol. 84(4):975-980.

Lippard, S.J., "Platinum complexes: Probes of polynucleotide structure and antitumor drugs," (1978) Accounts of Chemical Research 11:211-217.

(Continued)

Primary Examiner — Michael D Pak
(74) Attorney, Agent, or Firm — Quarles & Brady LLP

(57) ABSTRACT

The present invention relates, in general, to pattern-recognition receptors (PRRs), including toll-like receptors (TLRs), and, in particular, to a method of inhibiting nucleic acid-induced activation of, for example, endosomal TLRs using an agent that binds to the nucleic acid ("nucleic acid binding agent"), preferably, in a manner that is independent of the nucleotide sequence, the chemistry (e.g., DNA or RNA, with or without base or sugar modifications) and/or the structure (e.g., double-stranded or single-stranded, complexed or uncomplexed with, for example protein) of the nucleic acid(s) responsible for inducing TLR activation. The invention also relates to methods of identifying nucleic acid binding agents suitable for use in such methods.

5 Claims, 11 Drawing Sheets

(56) References Cited

OTHER PUBLICATIONS

Merai, Z. et al., "Double-stranded RNA binding may be a general plant RNA viral strategy to suppress RNA silencing," (2006) J. Virol. 80(12):5747-5756.
Oney, S. et al., "Development of universal antidotes to control aptamer activity," (2009) Nature Medicine, 15(10):1224-1229.
Que-Gewirth, N.S. et al., "Gene therapy progress and prospects: RNA aptamers," (2007) Gene Therapy 14(4):283-291.
Rusconi, C.P. et al., "RNA aptamers as reversible antagonists of coagulation factor IXa," (2002) Nature 419(5):90-94.
Rusconi, C.P. et al., "Antidote-mediated control of an anticoagulant aptamer in vivo," (2004) Nature Biotechnology 22(11):1423-1428.
Vollmer et al., "Characterization of three CpG oligodeoxynucleotide classes with distinct immunostimulatory activities", (2004) Eur. J. Immunol. 34:251-262.
White, R. R. et al., "Developing aptamers into therapeutics," (2000) J. Clin. Investigation 106(8):929-934.
Yu, P., "Nucleic Acid recognizing Toll-like recpetors as therapeutic targets: a focus on autoimmunity and cancer", Journal of Recpetor, (2009) Ligand and Channel Research 2:19-28.
International Search Report and Written Opinion for PCT/US2008/004119 dated Jun. 26, 2008.
International Search Report and Written Opinion for PCT/US2010/002516 dated Jun. 10, 2011.
Supplemental European Search Report dated Jun. 27, 2013 issued in connection with EP 10 81 7556.
Office Action dated Feb. 24, 2011 for U.S. Appl. No. 12/588,016.
Office Action dated Sep. 19, 2011 for U.S. Appl. No. 12/588,016.
Office Action dated Jul. 10, 2013 for U.S. Appl. No. 12/588,016.
Office Action dated Jul. 3, 2014 for U.S. Appl. No. 12/588,016.
Office Action dated Dec. 3, 2014 for U.S. Appl. No. 12/588,016.
Office Action dated Jun. 8, 2015 for U.S. Appl. No. 12/588,016.
Office Action dated Oct. 30, 2015 for U.S. Appl. No. 12/588,016.

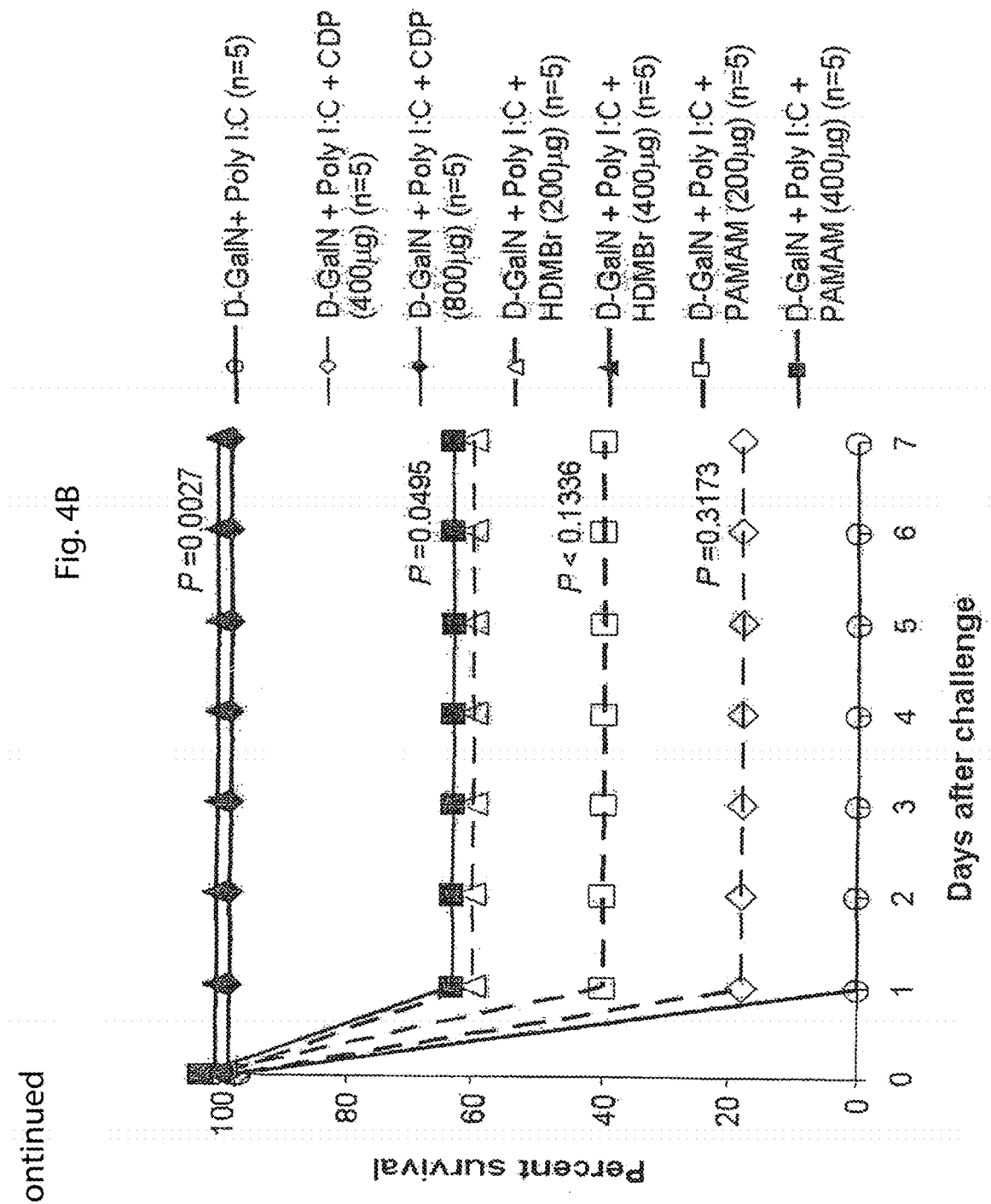
Figure 4, Continued

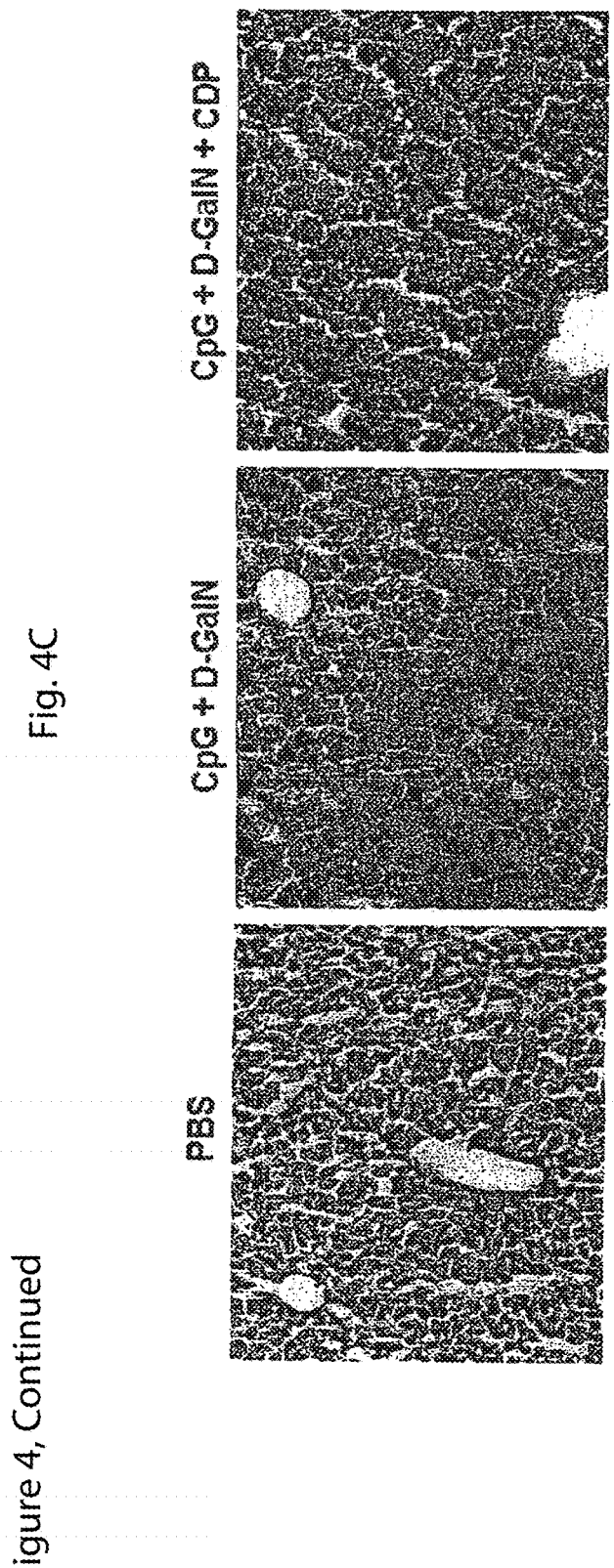
Figure 4, Continued

INHIBITION OF ENDOSOMAL TOLL-LIKE RECEPTOR ACTIVATION

This application is a continuation of U.S. application Ser. No. 13/496,313, filed Mar. 15, 2012 and issuing as U.S. Pat. No. 9,468,650 on Oct. 18, 2016, which patent is a U.S. National Phase Application of International Application No. PCT/US2010/002516, filed Sep. 16, 2010, which designated the U.S. and claims priority from U.S. Provisional Application No. 61/243,090, filed Sep. 16, 2009, the entire contents of each of which are hereby incorporated by reference.

This invention was made with government support under Grant No. HL65222 awarded by the National Institutes of Health. The Government has certain rights in the invention.

TECHNICAL FIELD

The present invention relates, in general, to pattern-recognition receptors (PRRs), including toll-like receptors (TLRs), and, in particular, to a method of inhibiting nucleic acid-induced activation of, for example, endosomal TLRs using an agent that binds to the nucleic acid ("nucleic acid binding agent"), preferably, in a manner that is independent of the nucleotide sequence, the chemistry (e.g., DNA or RNA, with or without base or sugar modifications) and/or the structure (e.g., double-stranded or single-stranded, complexed or uncomplexed with, for example protein) of the nucleic acid(s) responsible for inducing TLR activation. The invention also relates to methods of identifying nucleic acid binding agents suitable for use in such methods.

BACKGROUND

TLRs are type I transmembrane proteins composed of an extracellular 2 5 domain of leucine-rich repeats and an intracellular Toll/interleukin-1 (IL-1) receptor (TIR) domain (Leulier and Lemaitre, Nat. Rev. Genet. 9:165-178 (2008)). Ten human and twelve mouse TLRs have been identified. Each TLR is able to recognize a particular molecular pattern. For instance, TLR2, 4, 5, 6 and 11 bind to bacterial outer membrane molecules such as lipopolysaccharide (LPS), peptidoglycan and lipoteic acid while TLR3, TLR7, TLR8 and TLR9 recognize bacterial, viral or even endogenous nucleic acids (Kawai and Akira, Semin. Immunol. 19:24-32 (2007)). Moreover, TLRs can be classified based on their cellular localization: TLR1, 2, 4, 5 and 6 are expressed on the cell surface while TLR3, 7, 8 and 9 are localized mostly, though not exclusively, in endosomal compartments (Kawai and Akira, Semin. Immunol. 19:24-32 (2007)).

When pathogens invade a host, innate immune cells such as macrophages, neutrophils, natural killer cells and dendritic cells recognize pathogen-associated molecular patterns (PAMPs) and endogenous damage-associated molecular patterns (DAMPs) through TLRs. TLR activation initiates intracellular signaling events that result in the expression of immune response genes including inflammatory and immune modulatory cytokines, chemokines, immune stimulatory receptors, which augments killing of pathogens and initiates the process of developing acquired immunity (Takeda and Akira, Int. Immunol. 17:1-14 (2005), Akira et al, Cell 124:783-801 (2006)). Inappropriate activation of some members of the TLR family, on the other hand, contribute to development of a variety of diseases including bacterial sepsis (TLR1, TLR2, TLR3, TLR4 and TLR9) (Wurfel et al, Am. J. Respir. Crit. Care Med. 178:710-720 (2008), Knuefermann et al, Circulation 110:3693-3698 (2004), Cavassani et al, J. Exp. Med. 205:2609-2621 (2008), Alves-Filho et al, Crit. Care Med. 34:461-470 (2006), Tsujimoto et al, J. Hepatol. 45:836-843 (2006)), non-infection systemic inflammatory response syndrome (TLR4) (Breslin et al, Shock 29:349-355 (2008)), multiple sclerosis (TLR3, TLR4 and TLR9) (Chen et al, Int. Immunopharmacol 7:1271-1285 (2007)), systemic lupus erythematosus (SLE) (TLR7 and TLR9) (Marshak-Rothstein and Rifkin, Annu. Rev. Immunol. 25:419-441 (2007)) and rheumatoid arthritis (TLR3, TLR4, TLR7, TLR8 and TLR9) (Choe et al, J. Exp. Med. 197:537-542 (2003), O'Neil, Nat. Clin. Pract. Rheumatol. 4:319-327 (2008)). Moreover, preclinical and clinical studies indicate that inhibition of TLR activity has therapeutic benefits for treating certain diseases. For example, diverse LPS-neutralizing agents and TLR4 antagonists have been evaluated to treat inflammatory diseases in animal and clinical studies (Leon et al, Pharm. Res. 25:1751-1761 (2008)). A TLR9 inhibitor, inhibitory CpG DNA (Plitas et al, J. Exp. Med. 205:1277-1283 (2008)), and an antagonistic anti-TLR3 antibody (Cavassani et al, J. Exp. Med. 205: 2609-2621 (2008)) enhanced survival of a mouse with polymicrobial sepsis. Oligonucleotide-based TLR7 and TLR9 inhibitors prevented IFNα production from human plasmacytoid dendritic cells stimulated with serum from SLE patients (Barrat et al, J. Exp. Med. 202:1131-1139 (2005)). Unfortunately, the redundancy of the TLR family may limit the utility of inhibitors that target individual TLRs.

Upon stimulation, all TLRs recruit intracellular TIR-domain-containing adapters, such as TRIF and MyD88 (Kawai and Akira, Semin. Immunol. 19:24-32 (2007)). These adapter molecules mediate a downstream cascade of TLR-associated signaling. TRIF is recruited to TLR3 and TLR4, and appears to activate IRF3, MAPK, and NF-κB while MyD88 is associated with all TLRs, except TLR3, and phosphorylates IRAK, IRF5, IRF7, MAPK and NF-κB, which enhance the expression of type I IFN, inflammatory cytokine and IFN-inducible genes (Kawai and Akira, Semin. Immunol. 19:24-32 (2007)). Unlike other TLRs, endosomal TLRs, TLR3, 7, 8 and 9, all recognize microbial or host nucleic acids, as PAMPs or DAMPs, respectively. The redundancy and interconnectedness of the TLR signaling pathway suggests that it will be important to inhibit the activity of multiple TLRs simultaneously to effectively control inflammatory and autoimmune responses and to enhance the clinical efficacy of TLR antagonists as therapeutic agents.

It was discovered recently that certain cationic polymers are able to counteract the activity of a variety of oligonucleotide-based drugs (e.g., aptamers), irrespective of their nucleotide sequences (Oney et al, Control of Aptamer Activity by Universal Antidotes: An Approach to Safer Therapeutics, Nature Medicine (in press)). Moreover, immune stimulatory siRNA, a TLR7 agonist, condensed with a cyclodextrin-based polymer has been shown not to activate TLR7 (Hu-Lieskovan et al, Cancer Res. 65:8984-8992 (2005)). The present invention results, at least in part, from studies designed to determine whether agents that bind DNAs and RNAs in a sequence—independent manner (e.g., nucleic acid-binding cationic polymers) can neutralize endosomal TLR ligands and thereby inhibit activation of the corresponding TLRs.

SUMMARY OF THE INVENTION

The present invention relates generally to PRRs, including TLRs (e.g., endosomal TLRs). More specifically, the invention relates to a method of inhibiting nucleic acid-induced activation of, for example, endosomal TLRs using an agent that binds to the nucleic acid ("nucleic acid binding agent"), preferably, in a manner that is independent of the nucleotide sequence, the chemistry (e.g., DNA or RNA, with or without base or sugar modifications) and/or the structure (e.g., double-stranded or single-stranded, complexed or uncomplexed with, for example protein) of the nucleic acid responsible for inducing TLR activation. The invention further relates to methods of controlling inflammatory and/or autoimmune responses resulting from nucleic acid-induced receptor (e.g. endosomal TLR) activation using such a nucleic acid binding agent. The invention further relates to methods of identifying nucleic acid binding agents suitable for use in such methods.

Objects and advantages of the present invention will be clear from the description that follows.

BRIEF DESCRIPTION OF THE DRAWINGS

(FIG. 1A) The murine macrophage cell line, Raw264.7 was co-incubated in a 24-well microplate with a TLR9 agonist (CpG) (2 µM), a TLR3 agonist (poly I:C) (10 µg/ml) or a TLR4 agonist (LPS) (100 ng/ml) along with the cationic polymers, CDP, HDMBr, PAMAM, poly L-lysine or protamine (20 µg/ml) or PBS. Unmethylated GpC ODNs were used as a negative control for CpG. After 18-hours of incubation, culture supernatants were collected and analyzed for cytokines by ELISA. (FIG. 1B) The treated cells were tested for their expression of the co-stimulatory molecule CD86 using FACS. The light blue line represents PBS-treated cells. Green and red lines represent GpC-and CpG-treated cells, respectively. Data represents three individual experiments. Error bar is S.D.; n=3. * $P<0.005$ (both TNFα and IL-6; CpG or poly I:C+Cationic polymers vs CpG or Poly I:C alone); ✤ $P=0.0169$ and 0.0395 (TNFα and IL-6, respectively; poly I:C+CDP vs poly I:C alone); ✤ $P=0.0256$ and 0.0281 (TNFα and IL-6, respectively; poly I:C+protamine vs poly I:C alone).

(FIG. 2A) Cells were incubated with CpG (2 µM) in a 24-well microplate. CDP (20 µg/ml) was added at 0, ½, 1, 2, 4, 8 or 12 hours following the addition of CpG. At 24 hours after CpG treatment culture supernatants were collected and analyzed for TNFα and IL-6 production. (FIG. 2B) Cells were pre-incubated for 1 or 2 hours with CDP or PBS, washed three times with complete medium and then incubated in culture media supplemented with CpG. Simultaneous treatment of cells with CpG and CDP was used as a control. At 5 hours after CpG treatment the amount of TNFα in the culture supernatants were measured by ELISA. Error bar is S.D.; n=3. * $P<0.0001$ (both TNFα and IL-6; CpG+CDP vs CpG alone); ✤ $P=0.0230$ and $<0.0001$ (TNFα and IL-6, respectively; CpG+CDP vs CpG alone); ✤ $P=0.0257$ and 0.0003 (TNFα and IL-6, respectively; CpG+CDP vs CpG alone).

(FIG. 4A) Mice (5-10 mice/group) were i.p. injected with D-GalN (20 mg) alone, CpG (51 µg) alone, D-GalN+GpC (51 µg) or D-GalN+CpG (51 µg). After 5-10 minutes, PBS (100 µl), CDP (200 µg; blue diamond), HDMBr (200 or 400 µg; red triangle) or PAMAM (200 or 400 µg; green rectangle) was administered i.p. into mice challenged with D-GalN+CpG. Mice were monitored daily for survival. (FIG. 4B) Mixture of Poly I:C (200 µg) and D-GalN (20 mg) in PBS (100 µl) was injected i.p. into mouse (5 mice/group). Subsequently, PBS (100 µl; black circle), CDP (400 or 800 µg; blue diamond), HDMBr (200 or 400 µg; red triangle) or PAMAM (200 or 400 µg; green rectangle) was injected i.p. There is 5-10 minutes interval between injections. (FIG. 4C) Mice were injected with PBS, CpG+D-GalN or CpG+D-GalN+CDP. Sixteen hours following injection, liver specimens were collected for histological studies (hematoxylin and eosin staining). A representative of three individual results. Magnification ×20.

DETAILED DESCRIPTION OF THE INVENTION

Figures 1, 1A:
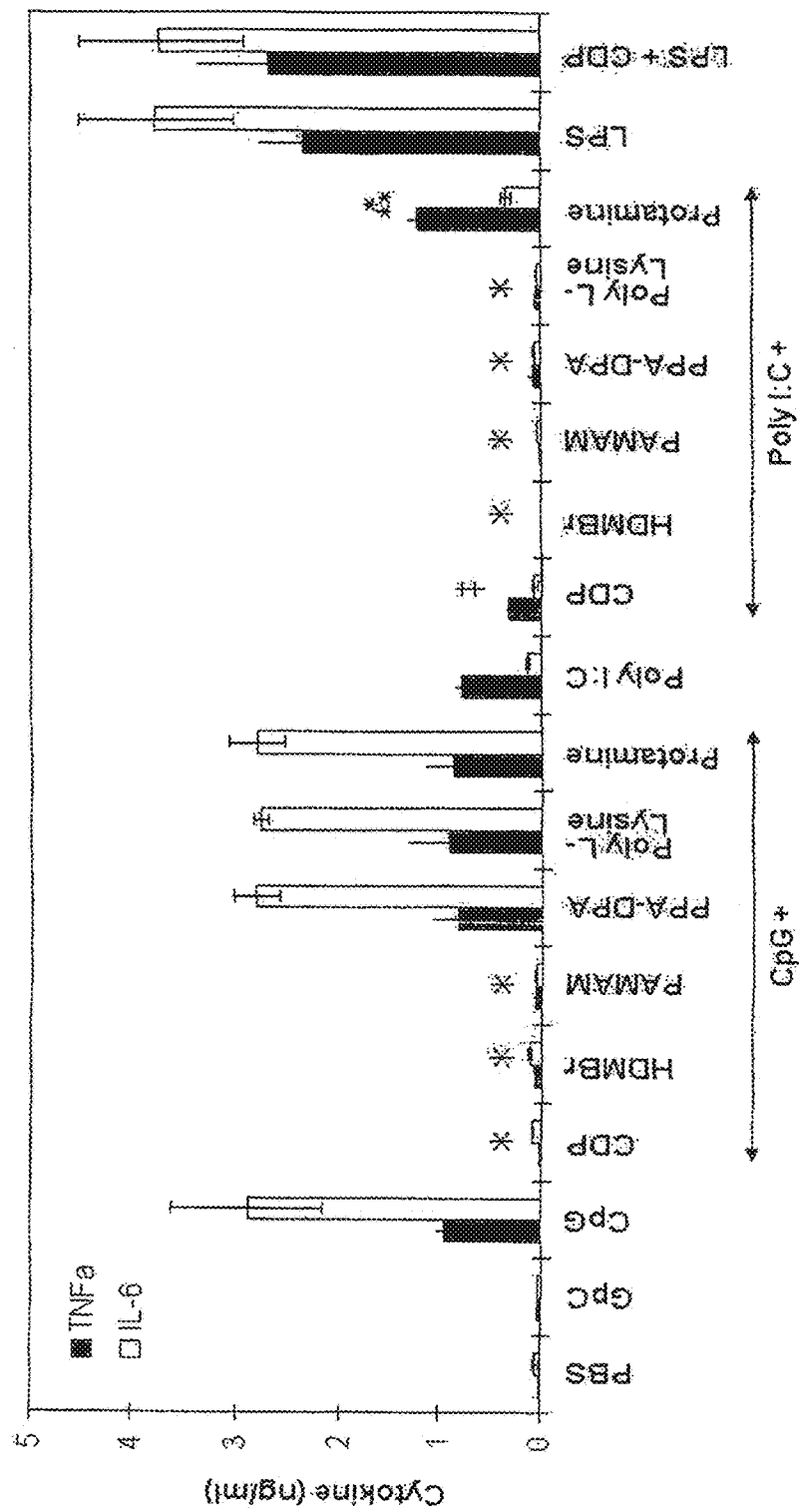
FIGS. 1A and 1B. Cationic polymers inhibit nucleic acid induced activation of TLR3 and TLR9.

PRRs are a pivotal component of host immune cells to protect tissues from various harmful stimuli, such as pathogens and damaged cells. A variety of PRRs, including RIG-I-like receptors (RLRs), dsRNA-dependent protein kinase R (PKR), DNA-dependent activator of IRFs (DAI) and TLRs can recognize diverse products of pathogens and damaged cells that are referred to PAMPs and DAMPs (Lotze et al, Immunol. Reviews 220:60-81 (2007)).

TLRs play a central role in host innate and acquired immunity, as well as in the pathogenesis of various diseases, including infectious diseases, inflammatory diseases and autoimmune diseases. TLRs 3, 7, 8 and 9 are localized in endosomes can be activated by microbial and host nucleic acids.

The present invention relates, in one embodiment, to a method of inhibiting nucleic acid-induced activation of endosomal TLRs. The method comprises administering to a patient in need thereof an agent that binds nucleic acids responsible for induction of TLR activation in an amount and under conditions such that inhibition of that activation is effected. Advantageously, the agent binds the nucleic acids in a manner that is independent of the nucleotide sequence, the chemistry (e.g., DNA or RNA, with or without base or sugar modifications) and/or the structure (e.g., double-stranded or single-stranded, complexed or uncomplexed with, for example, a protein) of the nucleic acids responsible for inducing TLR activation. The present method can be used to treat inflammatory and/or autoimmune responses resulting from endosomal activation.

Nucleic acid binding (scavenging) agents of the invention include pharmaceutically acceptable member(s) of a group of positively charged compounds, including proteins, lipids, and natural and synthetic polymers, that can bind nucleic acids in, for example, biologically fluids.

Proteinaceous nucleic acid binding agents of the invention include protamines, a group of proteins that yield basic amino acids on hydrolysis and that occur combined with nucleic acid in the sperm of fish, such as salmon. Protamines are soluble in water, are not coagulated by heat, and comprise arginine, alanine and serine (most also contain proline and valine and many contain glycine and isoleucine). In purified form, protamine has been used for decades to neutralize the anticoagulant effects of heparin. Nucleic acid binding agents of the invention also include protamine variants (e.g., the +18RGD variant (Wakefield et al, J. Surg. Res. 63:280 (1996)) and modified forms of protamine, including those described in Published U.S. Application No. 20040121443. Other nucleic acid binding agents of the invention include protamine fragments, such as those described in U.S. Pat. No. 6,624,141 and U.S. Published Application No. 20050101532. Nucleic acid binding agents of the invention also include, generally, peptides that modulate the activity of heparin, other glycosaminoglycans or proteoglycans (see, for example, U.S. Pat. No. 5,919,761). The invention further includes pharmaceutically acceptable salts of the above-described nucleic acid binding agents, as appropriate, including sulfate salts.

Proteinaceous nucleic acid binding agents of the invention also include DNA and/or RNA reactive antibodies. For example, anti-nuclear antibodies, such as those indicative of lupus erythematosis, Sjögren's syndrome, rheumatoid arthritis, autoimmune hepatitis, scleroderma, polymyositis and dermatomyositis, can be used. Specific examples of antibodies that recognize RNA/DNA include those described by Kitagawa et al (Mol. Immunol. 19(3):413-20 (1982)), Boguslawski et al (J. Immunol. Methods 89(1):123-30 (1986)), Williamson et al (Proc. Natl. Acad. Sci. 98(4): 1793-98 (2001)), and Blanco et al (Clin. Exp. Immunol. 86(1):66-70 (1991)).

In addition, heterogeneous nuclear ribonucleoproteins (HNRPs) can also be used in accordance with the invention. Cationic peptides that bind nucleic acids (e.g., in a sequence-independent manner) are suitable for use. For example, a chimeric peptide synthesized by adding nonamer arginine residues at the carboxy terminus of RVG (to yield RVG-9R) has been described by Kumar et al (Nature 448:39-43 (2007)). Viral proteins that package (e.g., coat) DNA or RNA (e.g., HIV gag protein), and peptides derived therefrom, can also be used in the present methods.

Cationic lipids can also be used as nucleic acid binding agents in accordance with the invention. Suitable cationic lipids include those described by Morille et al (Biomaterials 29:3477 (2008)) (e.g., linear poly(ethyleneimine) (PEI), poly(L-lysine) (PLL), poly(amidoamine) (PAMAM) dendrimer generation 4, chitosan, DOTMA, DOTAP, DMRIE, DOTIM, DOGS, DC-Chol, BGTC and DOPE).

Nucleic acid binding agents of the invention also include intercalating agents. Examples include ethidium bromide, proflavine, daunomycin, doxorubicin and thalidomide. Nucleic acid binding porphyrins can also be used in accordance with the invention (see Table 1).

Preferred nucleic acid binding agents of the invention include polycationic polymers. Preferred polycationic polymers include biocompatible polymers (that is, polymers that do not cause significant undesired physiological reactions) that can be either biodegradable or non-biodegradable polymers or blends or copolymers thereof. Examples of such polymers include, but are not limited to, polycationic biodegradable polyphosphoramidates, polyamines having amine groups on either the polymer backbone or the polymer side chains, nonpeptide polyamines such as poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly (N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride); natural or synthetic polysaccharides such as chitosan, cyclodextrin-containing polymers, degradable polycations such as poly[alpha-(4-aminobutyl)-L-glycolic acid] (PAGA); polycationic polyurethanes, polyethers, polyesters, polyamides, polybrene, etc. Particularly preferred cationic polymers include CDP, CDP-im, PPA-DPA, PAMAM and HDMBr.

Nucleic acid binding agents of the invention can include compounds of types described in Table 1, or derivatives thereof. Several of the compounds described in Table 1 contain cationic-NH groups permitting stabilizing charge-charge interactions with a phosphodiester backbone. Nucleic acid binding agents of the invention containing secondary amines can include, for example, 5-350 such groups (e.g., 5-300, 5-250, 5-200, 5-100, 5-50, 50-100, 50-200, 50-300, 50-350, 100-200, 100-300, 100-350, 200-350, 200-300, or 250-350), and can have a molecular weight in the range of, for example, 2,000 to 50,000 (e.g., 10,000 to 50,000 or 20,000 to 40,000).

TABLE 1

| Compound | Abbreviation | Molecular structure | Remark |
|---|---|---|---|
| Poly-L-lysine | PLL | $\text{+NH—CH—C+}_n$ with side chain $(CH_2)_4\text{—}NH_2$ and carbonyl $C=O$ | 1. Commercially available. 2. Carbonyl moiety (—C=O) which could permit additional stabilization to the complex through hydrogen bonds with DNA. |
| Poly-L-ornithine | PLO | $\text{+NH—CH—C+}_n$ with side chain $(CH_2)_3\text{—}NH_2$ and carbonyl $C=O$ | 1. Commercially available. 2. Carbonyl moiety (—C=O) which could permit additional stabilization to the complex through hydrogen bonds with DNA. |
| Polyphosphoramidate polymer series | PPA-SP PPA-BA PPA-EA PPA-MEA PPA-DMA PPA-DEA PPA-TMA PPA-DPA | $\text{+P(=O)(R)—O—CH(CH}_3\text{)—CH}_2\text{—O+}_n$    PPA<br><br>$R = H_2N\text{—}(CH_2)_3\text{—}N\text{—}(CH_2)_4\text{—}NH_2$    PPA-SP<br>—NH—(CH$_2$)$_4$—NH$_2$    PPA-BA<br>—NH—(CH$_2$)$_2$—NH$_2$    PPA-EA<br>—NH—(CH$_2$)$_2$—NH—CH$_3$    PPA-MEA | 1. Polymers with an identical backbone but different side chains ranging from primary to quaternary amines Provide a platform for a systematic study. 2. Lower cytotoxicity compared with polyethylenimine (PEI) and poly-L-lysine (PLL). |

TABLE 1-continued

| Compound | Abbreviation | Molecular structure | Remark |
|---|---|---|---|
| | | —NH—(CH$_2$)$_2$—N(CH$_3$)(CH$_3$)<br>PPA-DMA | |
| | | —NH—(CH$_2$)$_2$—N(CH$_2$CH$_3$)(CH$_2$CH$_3$)<br>PPA-DEA | |
| | | —NH—(CH$_2$)$_2$—N$^{\oplus}$(CH$_3$)(CH$_3$)(CH$_3$)<br>PPA-TMA | |
| | | N((CH$_2$)$_3$—NH$_2$)((CH$_2$)$_3$—NH$_2$)<br>PPA-DPA | |
| Polyphosphoramidate diprophylamine- poly ethylene glycol copolymer | PPA-DPA-b-PEG$_{2000}$ | PEG—(O—P(=O)(O—CH(CH$_3$)—CH$_2$—O)—N((CH$_2$)$_3$—NH$_2$)((CH$_2$)$_3$—NH$_2$))$_n$ | 1. a copolymer of PPA-DPA and PEG. |
| Polyethyleneimine | PEI | —(CH$_2$—CH$_2$—NH)$_n$— | 1. Commercially available.<br>2. PEI with branched structure condenses DNA to a greater extent than linear ones.<br>3. high cytotoxicity. |
| Ionene e.g. polybrene | | —N$^{\oplus}$(CH$_3$)(CH$_3$)—(CH$_2$)$_3$—N$^{\oplus}$(CH$_3$)(CH$_3$)—(CH$_2$)$_6$—)$_n$<br>2 Br$^{\ominus}$ | 1. Commercially available.<br>2. Have high charge density. |

TABLE 1-continued

| Compound | Abbreviation | Molecular structure | Remark |
|---|---|---|---|
| Natural polyamine e.g. Putrescine Spermine Spermidine | | $H_2N-(CH_2)_4-NH_2$ <br> $H_2N-(CH_2)_3-NH-(CH_2)_4-NH-(CH_2)_3-NH_2$ <br> $H_2N-(CH_2)_4-NH-(CH_2)_3-NH_2$ | 1. Commercially available. <br> 2. The most extensive work on their binding with DNA has been carried out and have remarkable effects on the DNA condensation. |
| Poly(allylamine) | PAL | $-(CH_2-CH)_n-$ <br> $\hspace{1em}|$ <br> $\hspace{1em}CH_2$ <br> $\hspace{1em}|$ <br> $\hspace{1em}NH_2$ | 1. Commercially available. <br> 2. Highly positive charged <br> 3. Low toxicity. |
| Peptide nucleic acid | PNA | 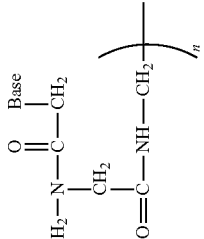 | 1. Commercially available. <br> 2. Binding through Watson-crick base pairing, thus binding is typically stronger and more rapid. |
| Water soluble porphyrin e.g. poly tetra(p-aminophenyl) porphyrin poly tetra (methylpyridine) porphyrin | $H_2TAPP$ <br> $H_2TMPyP_4$ | 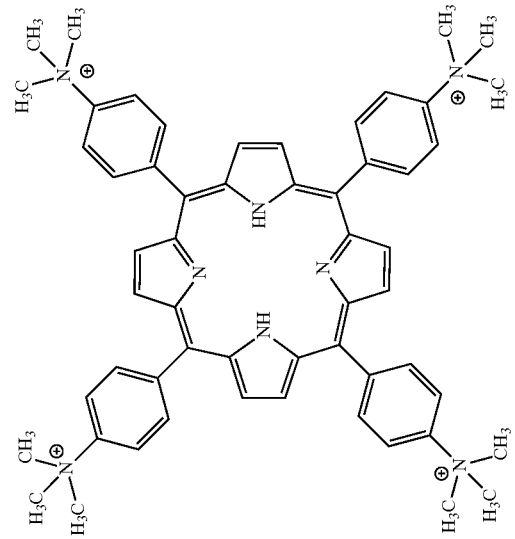 | 1. Commercially available. <br> 2. One or two $-N^+(CH_3)_3$ groups of one TAPP molecule bind with the phosphate groups. <br> 3. The stacking of TAPP along the surface of DNA leads to a favorite binding. <br> 4. Especially good binding with G-quadruplex through pi-pi interaction. |

TABLE 1-continued
| Compound | Abbreviation | Molecular structure | Remark |
|---|---|---|---|
| Poly(porphyrin) or Porphyrin ladder | e.g. poly(H$_2$(p-TAPP)-poly(por)A-AN)) | 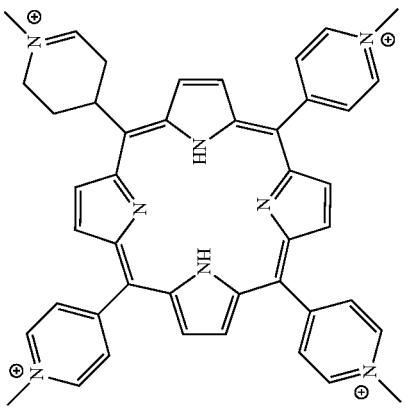 | |

TABLE 1-continued

| Compound | Abbreviation | Molecular structure | Remark |
|---|---|---|---|
| Poly (N,N-dimethylacrylamide) | PDMA | ![structure] | |
| Poly (2-Methacryloyloxyethyl phosphorylcholine) | PMPC | ![structure] | |
| Dendrimers | | | |

TABLE 1-continued

| Compound | Abbreviation | Molecular structure | Remark |
|---|---|---|---|
| e.g. polyamidoamine dendrimer | PAMAM Dendrimer G2 | 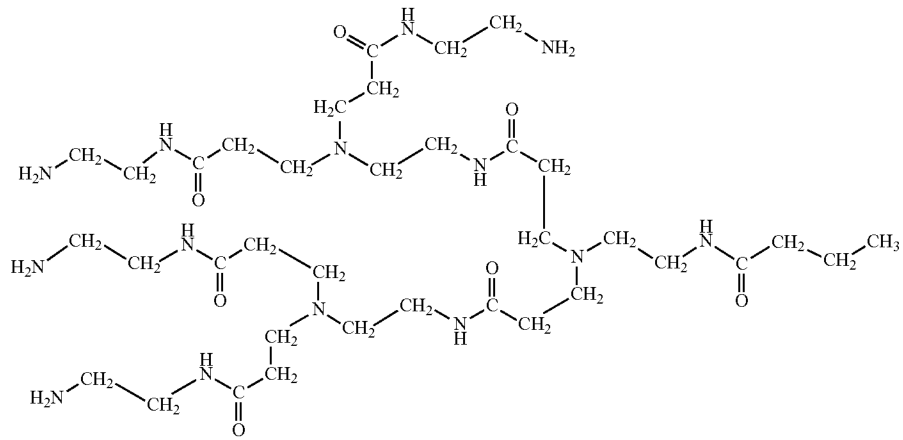 [SMILES: CCCC(=O)NCCN(CCC(=O)NCCN(CCC(=O)NCCN)CCC(=O)NCCN)CCC(=O)NCCN(CCC(=O)NCCN)CCC(=O)NCCN] | 1. Commercially available.<br>2. Branched spherical shape and a high density surface charge.<br>3. Low cytotoxicity. |
| e.g. polypropyleneimine dendrimer | PPI dendrimer | 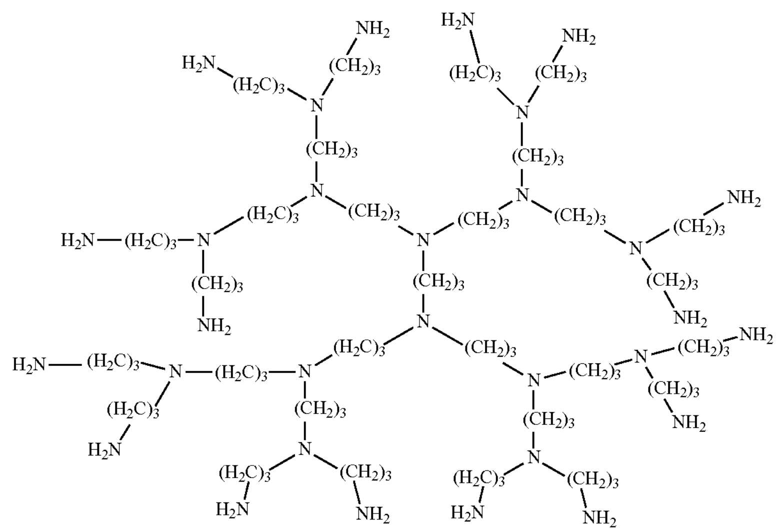 | 1. A class of amine-terminated polymers, demonstrated to be efficient gene delivery vectors.<br>2. Low cytotoxicity in a wide range of mammalian cell lines.<br>3. Unique molecular structures, with defined molecular weight, surface charge and surface functionality. These properties of dendrimers provide a platform for a systematic study. |

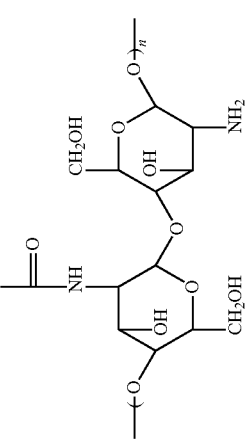

TABLE 1-continued
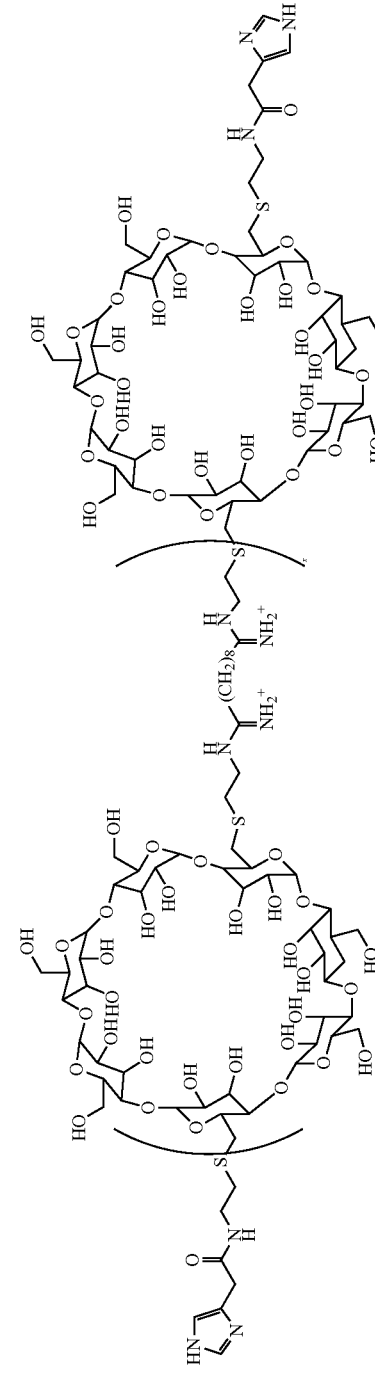
| Compound | Abbreviation | Molecular structure | Remark |
|---|---|---|---|
| Cyclo-dextrin Containing Polymers | CDP | 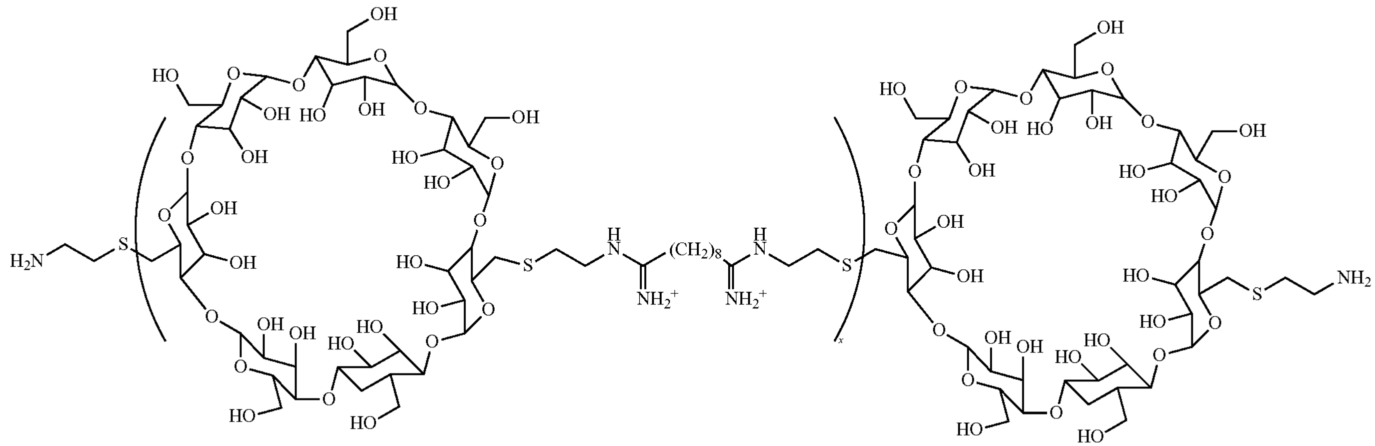 | |
| | CDP-Im | | |

Advantageously, the binding affinity of a nucleic acid binding agent of the invention for a nucleic acid, expressed in terms of Kd, is in the pM to :M range, preferably, less than or equal to 50 nM; expressed in terms of binding constant (K), the binding affinity is advantageously equal to or greater than $10^5 M^{-1}$, preferably, $10^5 M^{-1}$ to $10^8 M^{-1}$, more preferably, equal to or greater than $10^6 M^{-1}$. Thus, the binding affinity of the sequence-independent nucleic acid binding agents can be, for example, about $1\times10^5$ $M^{-1}$, $5\times10^5$ $M^{-1}$, $1\times10^6$ $M^{-1}$, $5\times10^6$ $M^{-1}$, $1\times10^7$ $M^{-1}$, $5\times10^7$ $M^{-1}$; or about 10 pM, 100 pM, 1 nM, 10 nM, 100 nM, 1 µM, 10 µM, 100 µM. "K" and "Kd" can be determined by methods known in the art, including surface plasmon resonance or a real time binding assay such as Biacore.

Preferred nucleic acid binding agents of the invention simultaneously limit the activation of multiple endosomal TLRs (e.g., TLR3 and TLR9). Particularly preferred are CDP or CDP-im, HDMBr and PAMAM (see U.S. Pat. Nos. 7,270,808, 7,166,302, 7,091,192, 7,018,609, 6,884,789, 6,509,323, 5,608,015, 5,276,088, 5,855,900, U.S. Published Appln. Nos. 20060263435, 20050256071, 200550136430, 20040109888, 20040063654, 20030157030, Davis et al, Current Med. Chem. 11(2) 179-197 (2004), and Comprehensive Supramolecular Chemistry vol. 3, J. L. Atwood et al, eds, Pergamon Press (1996)).

As indicated above, the present invention provides a method of controlling (inhibiting or preventing) autoimmune and/or inflammatory responses associated with activation of TLRs (e.g., endosomal TLRs such as TLR3 and TLR9). Such responses play a role in the pathogensis of diseases/disorders that are associated with presence in the circulation of the patient of free nucleic acids, either pathogen-derived (e.g., viral- or bacterial-derived) nucleic acids or nucleic acids released from dead or damaged host cells. Specific diseases/disorders that can be treated using nucleic acid binding agents of the invention include infectious diseases, cardiovascular disease, cancer, bacterial sepsis, multiple sclerosis, systemic lupus erythematosis, rheumatoid arthritis, COPD, obesity and psoriasis.

RLRs are a family of cytoplasmic RNA helicases including retinoic-acid-inducible protein I (RIG-I) and melanoma-differentiation-associated gene 5 (MDA5). RIG-I recognize uncapped 5'-triphosphate ssRNA and short dsRNA while MDA5 recognize long dsRNA (Pichlmair et al, Science 314:997-1001(2006), Hornung et al, Science 314:994-997 (2006), Kato et al, J. Exp. Med. 205:1601-1610 (2008)). Signaling of RLRs is initiated by interaction of caspase recruitment domain (CARD)-containing adapter molecule, IFNβ promoter stimulator-1 (IPS-1), and induce production of type I IFN and inflammatory cytokines (Kawai et al, Ann. N. Y. Acad. Sc. 1143:1-20 (2008)). PKR is an IFN-inducible cytosolic enzyme and recognizes viral dsRNAs while DAI recognizes cytoplasmic dsDNA (Langland et al, Virus Res 119:100-110 (2006), Takaoka et al, Nature 448:501-505 (2007)). These cytoplasmic PRRs, including RIG-I, MDA5 and PKR, are able to recognize RNAs or DNAs and activation of these PRRs is associated with type I IFN production. Although their involvement in the pathogenesis of inflammatory and autoimmune diseases has not been fully elucidated, the cytoplasmic nucleic acid-sensing PRRs may also contribute to the pathogenesis of such diseases because signaling from these receptors robustly elicits production of IFN∀, one of the major pathogenic factors in a variety of inflammatory diseases (J. Banchereau et al, Immunity 20:539-550 (2004)). Therefore, the present invention also relates a method of inhibiting nucleic-acid induced activation of these members of the PRR family using the approaches and agents described above.

Another application of nucleic acid-binding agents (scavengers) described herein is to counteract the effects of DNA and RNA molecules that are released from cells and subsequently induce thrombosis (Kannemeier et al, Proc. Natl. Acad. Sci. 104:6388-6393 (2007); Fuchs et al, Proc. Natl. Acad. Sci. Published Online before Print Aug. 23, 2010). Recently it has been observed that RNA and DNA molecules can activate the coagulation pathway as well as platelets and thereby engender blood clotting (Kannemeier et al, Proc. Natl. Acad. Sci. 104:6388-6393 (2007); Fuchs et al, Proc. Natl. Acad. Sci. Published Online before Print Aug. 23, 2010). Since nucleic acid binding agents (scavengers) described herein can bind RNA and DNA molecules and shield them from other potential binding partners, such agents can be employed to inhibit the ability of DNA and RNA molecules to bind and activate coagulation factors and platelets. In so doing, these RNA/DNA scavengers can be utilized to limit nucleic acid-induced pathological blood coagulation. Thus nucleic acid binding agents (scavengers) described herein represent novel entities for preventing the induction and progression of a variety of thrombotic disorders including myocardial infarction, stroke and deep vein thrombosis.

The nucleic acid binding agents of the invention, or pharmaceutically acceptable salts thereof, can be administered to the patient via any route such that effective levels are achieved in, for example, the bloodstream. The optimum dosing regimen will depend, for example, on the nucleic acid binding agent, the patient and the effect sought. Typically, the nucleic acid binding agent will be administered orally, transdermally, IV, IM, IP or SC. The nucleic acid binding agent can also be administered, for example, directly to a target site, for example, directly to a tumor (e.g., a brain tumor) when cancer is the disease to be treated. Advantageously, the nucleic acid binding agent is administered as soon as clinical symptoms appear and administration is repeated as needed.

The nucleic acid binding agents (including nucleic acid binding polymers incorporated into microparticles or nanoparticles or beads), or pharmaceutically acceptable salts thereof, can be formulated with a carrier, diluent or excipient to yield a pharmaceutical composition. The precise nature of the compositions of the invention will depend, at least in part, on the nature of the nucleic acid binding agent and the route of administration. Optimum dosing regimens can be readily established by one skilled in the art and can vary with the nucleic acid binding agent, the patient and the effect sought.

Proteinaceous nucleic acid binding agents of the invention can also be produced in vivo following administration of a construct comprising a sequence encoding the proteinaceous nucleic acid binding agent (Harrison, Blood Rev. 19(2):111-23 (2005)).

It will be appreciated that the treatment methods of the present invention are useful in the fields of both human medicine and veterinary medicine. Thus, the patient (subject) to be treated can be a mammal preferably a human. For veterinary purposes the subject can be, for example, a farm animal such as a cow, pig, horse, goat or sheep, or a companion animal such as a dog or a cat.

The invention also relates to methods of identifying nucleic acid binding agents suitable for use in the above-described methods. In one embodiment, endosomal TLR-containing cells, preferably, mammalian cells (e.g., mammalian macrophage cells in culture), are incubated with a first endosomal TLR agonist (e.g., CpG DNA or single or double stranded RNA or nucleic acid-containing particles) in the presence and absence of a test agent. Following incubation, a culture supernatant sample can be taken and analyzed for the presence of a product of an intracellular signaling event initiated by TLR activation, for example, one or more cytokines (e.g., TNFα and/or IL-6). These steps can be repeated with an endosomal TLR agonist having a sequence, chemistry and/or structure different from that of the first agonist. A test agent that inhibits endosomal TLR agonist activation, preferably, in a manner independent of the sequence, chemistry and/or structure of the endosomal TLR agonist used, (that inhibition of activation being evidenced by inhibition of production of a product of an intracellular signaling event initiated by TLR activation (e.g., cytokine production) (e.g., in a dose dependent manner)) can then be tested in vivo, for example, in mice, to further assess its suitability for use in the methods described herein.

Certain aspects of the invention can be described in greater detail in the non-limiting Example that follows.

EXAMPLE

Experimental Details

Animal and cell line studies. 8-9 weeks old C57BL/6 mice were purchased from the Jackson Laboratory (Bar Harbor, Me.). The murine macrophage cell line, Raw264.7 was obtained from ATCC (Manassas, Va.).

Cytokine production of murine macrophage. $1 \times 10^6$ Raw264.7 cells were cultured in complete medium including DMEM with 10% heat-inactivated FBS, penicillin, streptomycin and L-glutamine (2 mM) (all from Invitrogen, Carlsbad, Calif.) in a 24-well culture plate at 37° C. in a humidified atmosphere with 5% $CO_2$. To study TLR activation, the complete medium was supplemented with phosphorothioate B-type CpG DNA 1668 (5'-TC-CATGACGTTCCTGATGCT-3'), a phosphorothioate GpC DNA 1720 (5'-TCCATGAGCTTCCTGATGCT-3') as a control CpG DNA (both from IDT, Coralville, Iowa) or a mimetic of viral dsRNA, poly I:C (Amersham/GE Healthcare, Piscataway, N.J.) at various concentrations. Bacterial LPS serotype 026:B6 (100 ng/ml) (Sigma-Aldrich, Saint Louis, Mo.) activating TLR4 were used as a non-nucleotide-based TLR ligand. To block TLR activation CDP (Calando Pharmaceuticals, Pasadena, Calif.), protamine (APP, Schaumburg, Ill.), PPA-DPA, PAMAM, poly-L-lysine or HDMBr (polybrene) (kindly provided by Dr. Kam W. Leong, Duke University, Durham, N.C.) at various concentrations were simultaneously treated with either CpG DNA or poly IC. After 18 hours of incubation, culture supernatant were collected and stored at −80° C. for later analyses. The production of TNFα and IL-6 were analyzed with BD OptEIA™ ELISA sets (BD Biosciences, Franklin Lakes, N.J.) by following the manufacturer's instructions.

Co-stimulatory molecule expression on macrophage. $1 \times 10^6$ Raw264.7 cells were cultured with phosphate buffer saline (PBS), GpC DNA (2 μM) or CpG DNA (2 μM). To block binding of CpG DNA and TLR9 CDP, HDMBr, PAMAM, PPA-DPA, poly-L-lysine or protamine (20 t.g/ml each) were co-treated with CpG DNA. After 18 hours, cells were detached from plates by treatment of 0.05% Trypsin-EDTA (Invitrogen), washed twice with PBS and stained with either phycoerythrin (PE)-anti-mouse CD86 (GL1) or PE-rat IgG2a, κ as an isotype control (all from eBioscience, San Diego, Calif.). Cells were washed with PBS, fixed with 4% formaldehyde, and analyzed on a FACS Caliber (BD Biosciences).

Mouse TLR-mediated acute liver injury. TLR3 or TLR9-mediated acute liver injury in a D-galactosamine-sensitized mice was performed as previously described (Alexopoulou et al Nature 413:732-738 (2001), Duramad et al, J. Immunol. 174:5193-5200 (2005)). Briefly, C57BL/6 mice were injected intraperitoneally (i.p.) with PBS (100 μl), CpG DNA (25 to 51 μg), GpC DNA (50 μg) or poly I:C (50 to 200 μg) with or without D(+)Galactosamine, Hydrochloride (D-GalN) (EMD Biosciences, La Jolla, Calif.) (20 mg). Five to ten minutes after toxin challenge, cationic molecules (200 to 800 μg) were injected i.p. Viability of mice was monitored for a week.

Histopatholoy. Liver lobes were excised from mice 24 hours after injection of CpG+D-GalN with or without cationic molecules. The liver specimens were fixed with 4% formaldehyde, embedded in OCT and sectioned at a thickness of 20 μm before staining with hematoxylin and eosin for light microscopic examination.

Statistical Analysis. The difference of cytokine production among experimental groups was compared by the paired two-tailed Student's t test analyzed with Microsoft Office Excel 2003. Significance of survival was determined by the log-rank test analyzed with GraphPad Prism® Version 4.0b. A probability of less than 0.05 (P<0.05) was used for statistical significance.

Results

Figure 1B:
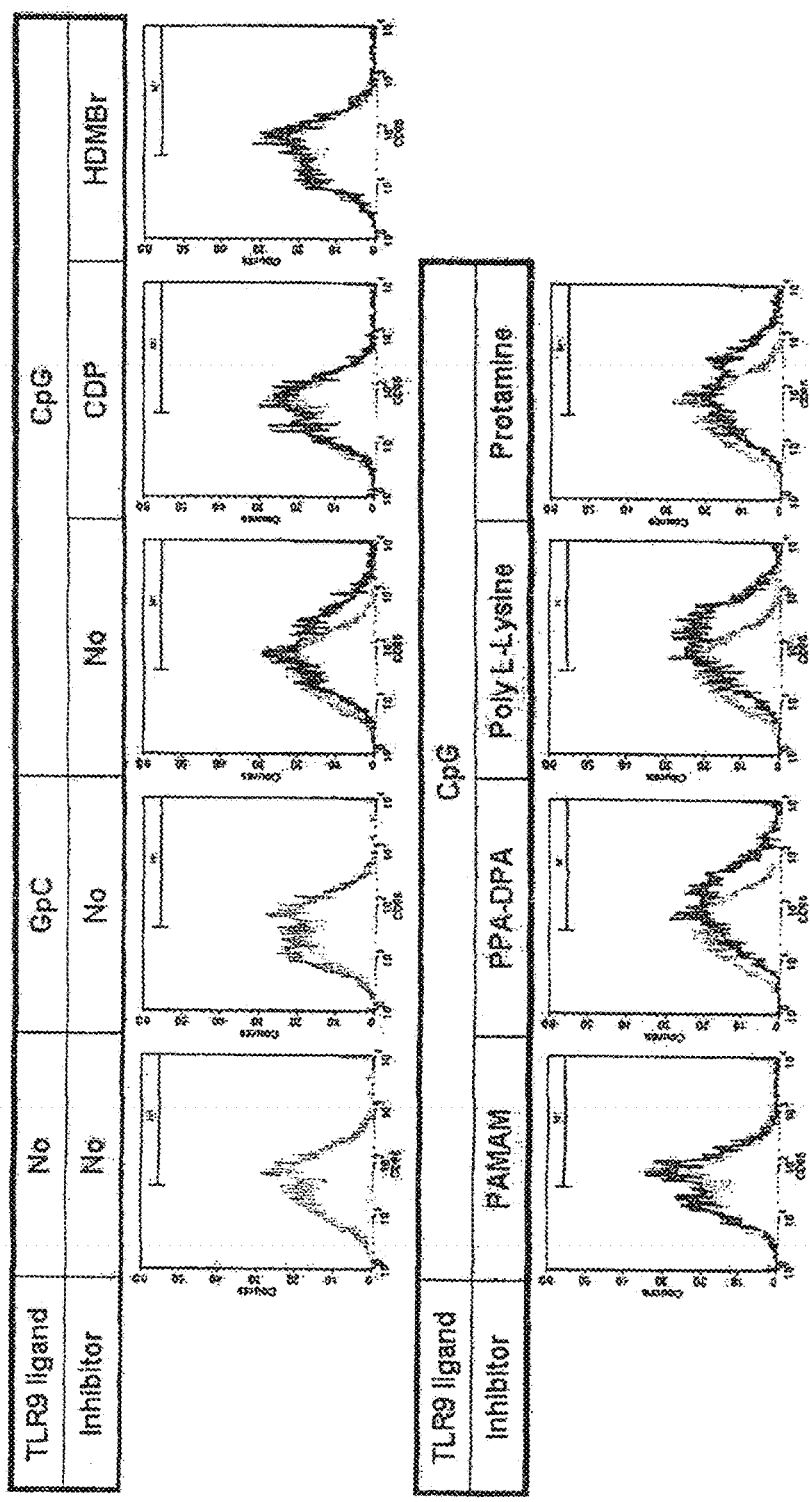
Figure 2:
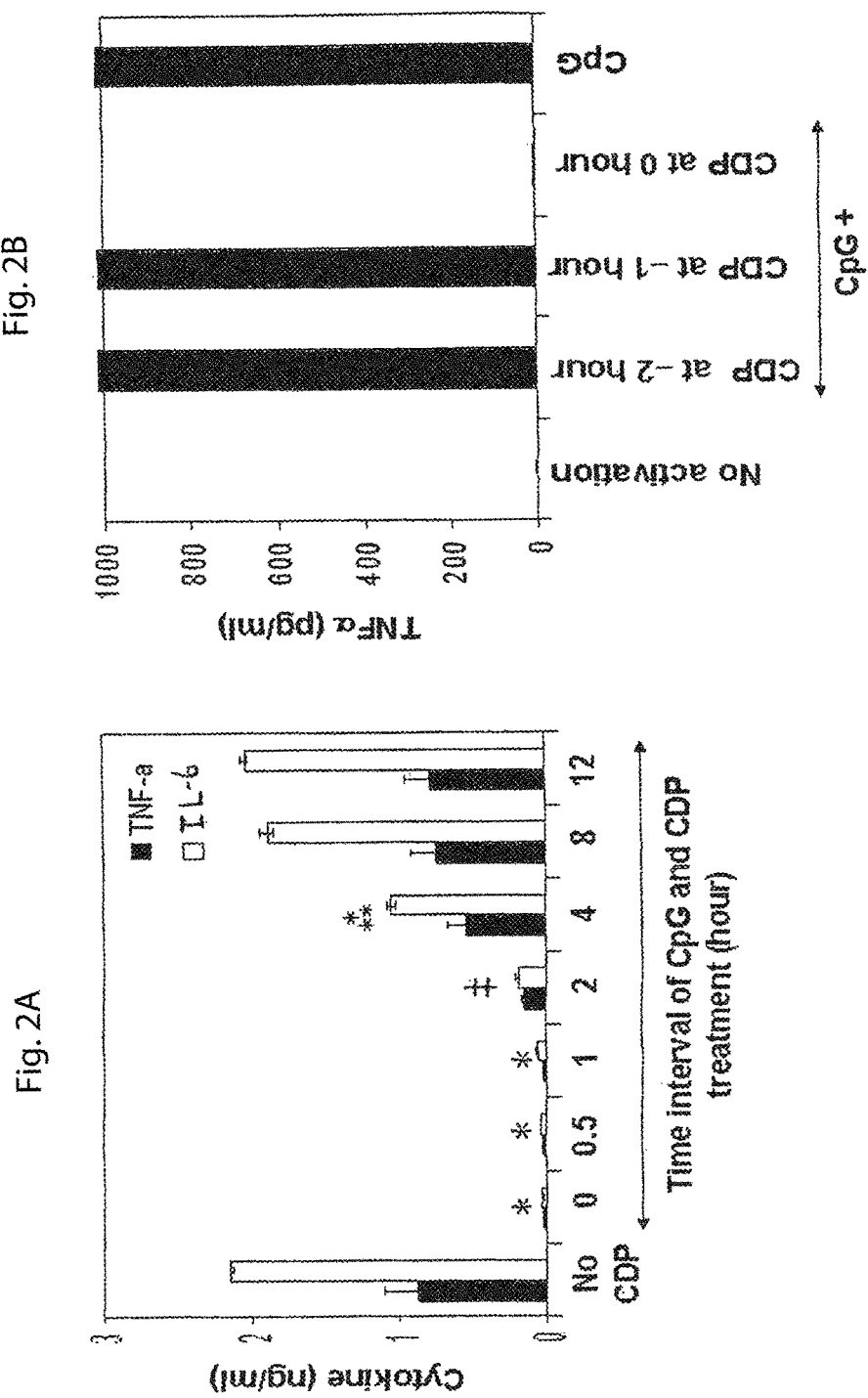
FIGS. 2A and 2B. Timing of cationic polymer mediated inhibition of TLR activation.

Six agents known to bind nucleic acids were evaluated for their ability to attenuate endosomal TLR responses: β-cyclodextrin-containing polycation (CDP), polyphosphoramidate polymer (PPA-DPA), polyamidoamine dendrimer, 1,4-diaminobutane core, G3 (PAMAM), poly-L-lysine, hexadimethrine bromide (HDMBr; also known as polybrene) and protamine. Five of the compounds inhibited polyinosinic-polycytidylic acids (poly I:Cs), a dsRNA activator of TLR3, stimulation of macrophages as measured by TNFα and IL-6 production and three prevented inflammatory cytokine production from the cells stimulated with unmethylated CpG DNA, a TLR9 agonist (FIG. 1A). The CpG DNA-inhibitory cationic polymers also impeded the up-regulation of co-stimulatory molecules expressed on macrophages (FIG. 1B). Interestingly, the inhibitors could be administered up to 4 hours after the CpG DNA and still significantly reduce TNFα and IL-6 production from macrophages (FIG. 2). Pre-treatment of macrophages with CDP, however, did not alter the ability of the cells to produce inflammatory cytokines (FIG. 2). By contrast, the nucleic acid-binding cationic polymers did not inhibit LPS-mediated activation of macrophages, which indicates that they specifically interfere with recognition of nucleic acids by TLRs.

Figures 3, 3A:
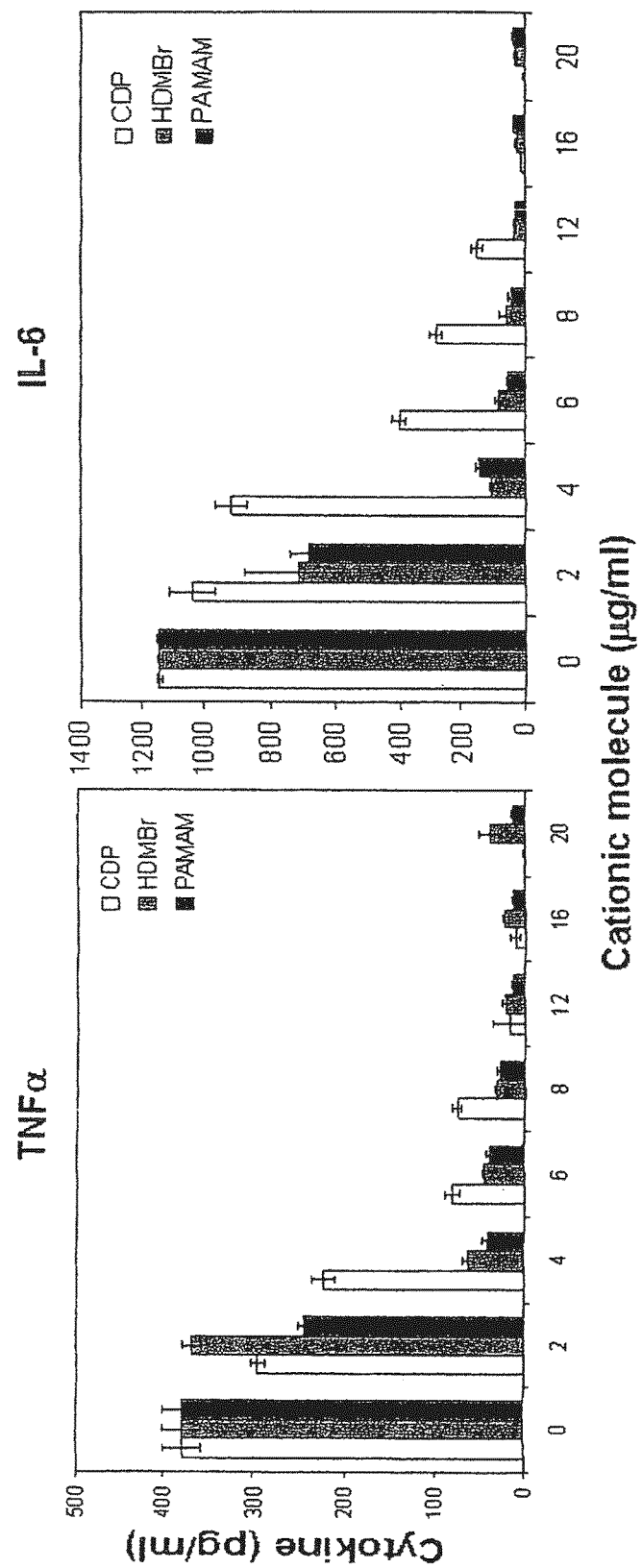
FIGS. 3A and 3B. Dose-dependent inhibition of cationic molecules on TLR3 and TLR9 activation. $1\times10^6$ Raw264.7 cells were cultured for 18 hours with either CpG (1 µM) (FIG. 3A) or poly I:C (10 µg/ml) (FIG. 3B) in the presence or absence of CDP (□), HDMBr (▨) or PAMAM (■) at the indicated concentration. Amounts of TNFα and IL-6 in the culture supernatant were measured by ELISA. Error bar is S.D.; n=3. NT: not tested.
Figure 3B:
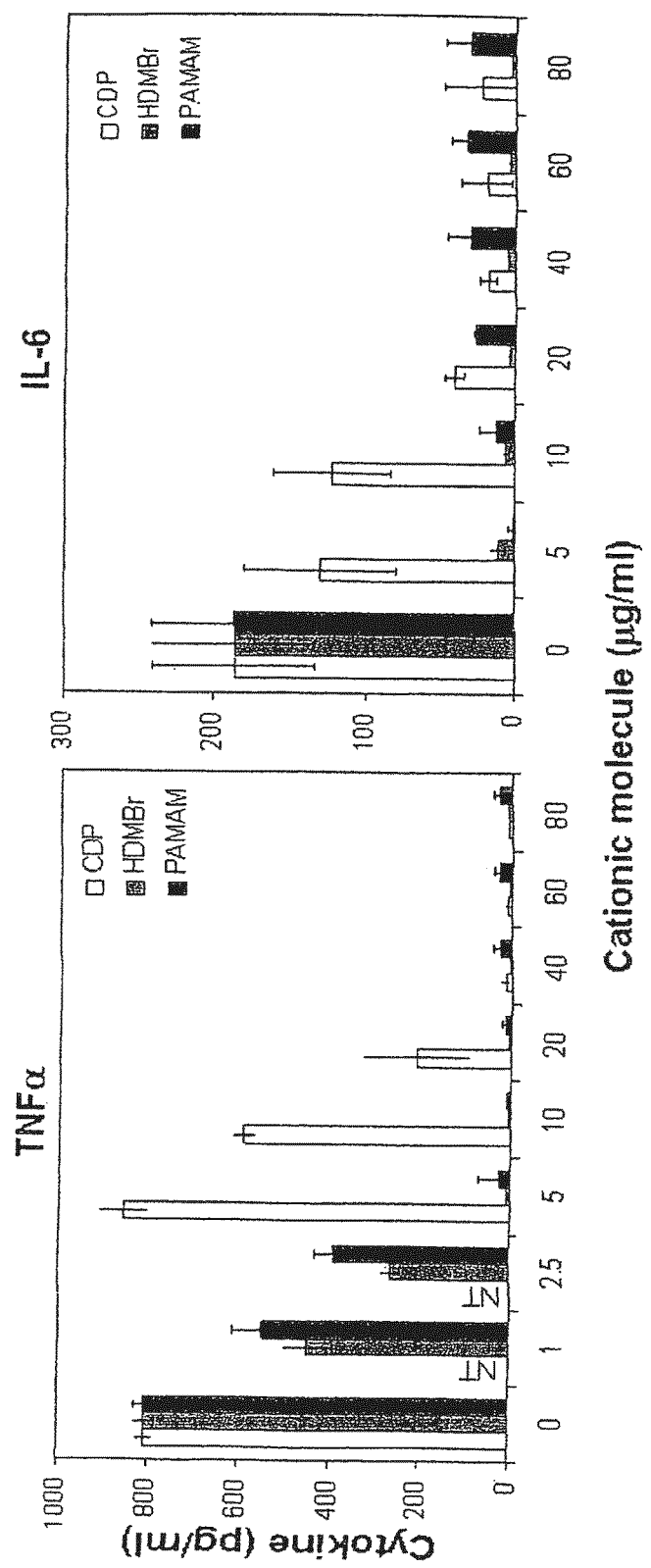
Figure 5:
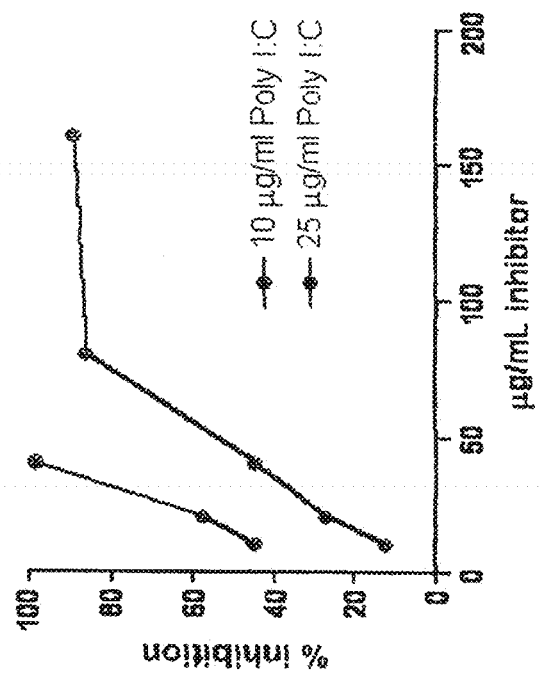
FIGS. 5A and 5B. Stoichiometry of TLR inhibition of CDP. Raw264.7 cells were cultured for 18 hours with either CpG (1 µM, 2 µM, 4 µM, 8 µM) (FIG. 5A) or poly I:C (10 µg/ml or 25 µg/ml) (FIG. 5B). TLR ligands were simultaneously supplemented with CDP at various concentration (0, 4, 8, 12, 16, 20, 24, 36, 48 µg/ml for CpG; 0, 10, 20, 30,40, 80, 160 µg/ml for poly I:C). Amount of TNFα was measured by ELISA. % inhibition was calculated by ([CpG or poly I:C]-[CpG or poly I:C+CDP])/[CpG or poly I:C]×100.
Figure 5:
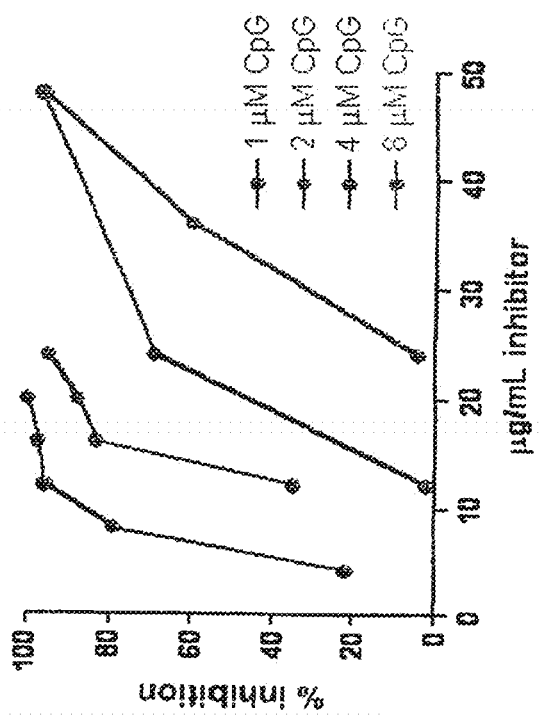

The nucleic acid-binding polymers inhibit TLR3 and TLR9 activation in a dose-dependent manner. A dose-escalation study demonstrated that 8 to 12 μg/ml of the polymers, CDP, HDMBr and PAMAM, which inhibited the activation of both TLR3 and TLR9, can inhibit inflammatory cytokine production by greater than 95% from macrophages treated with CpG DNAs (1 μM) and 5 to 40 μg/ml of these same polymers can reduce cytokine production by greater than 95% from cells treated with poly I:C (10 μg/ml) (FIGS. 3A and 5).

Figure 6:
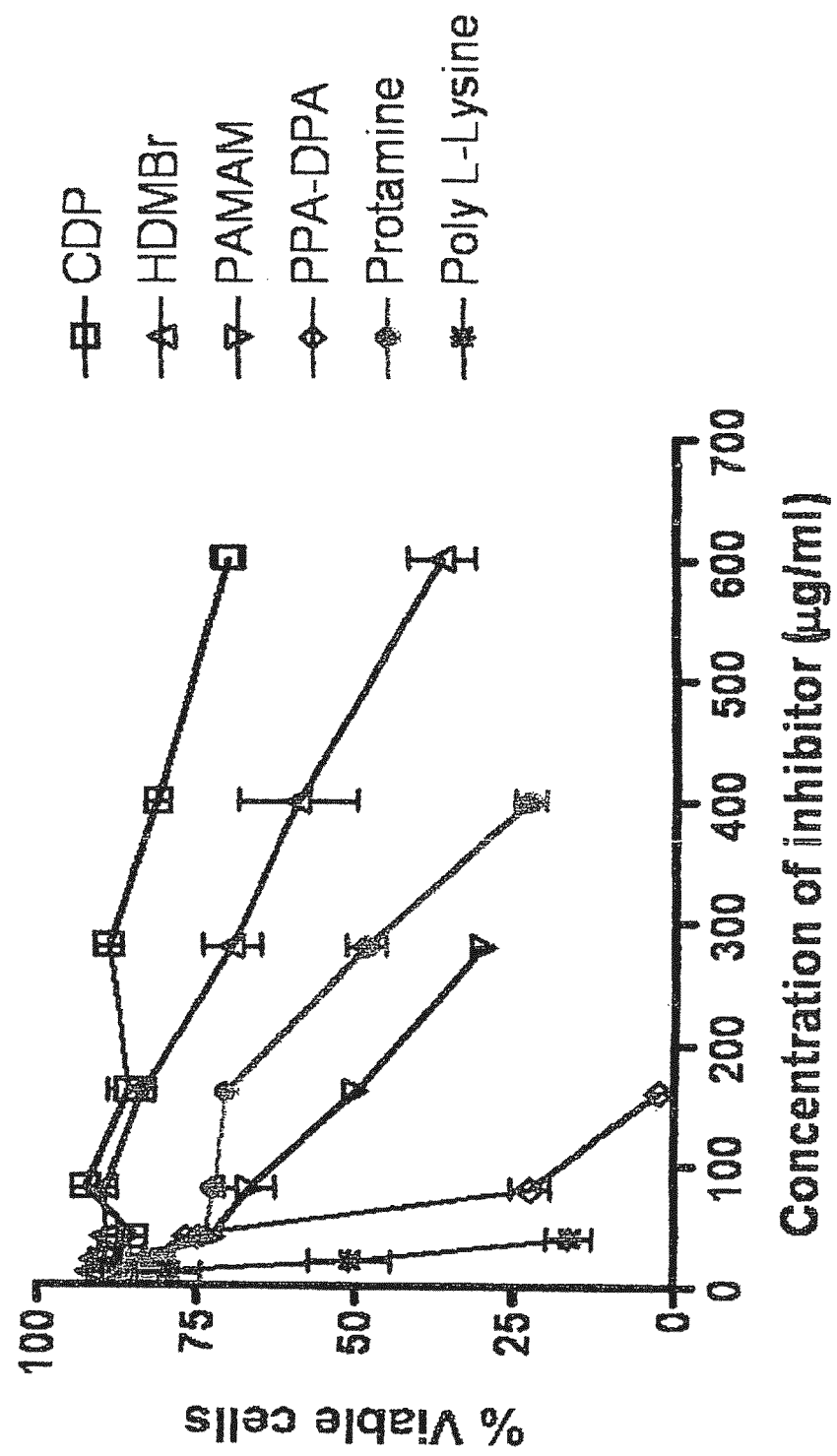
FIG. 6. Cellular toxicity of cationic molecules. $1\times10^6$ Raw264.7 cells were cultured for 24 hours with CDP (black), HDMBr (red), PAMAM (blue), PPA-DPA (green), protamine (gray) or poly L-lysine (purple) at various concentration (10, 20, 40, 80, 160, 280, 400 and 600 µg/ml). Viability of cells was analyzed using hematocytometer after staining with trypan blue (Sigma, St. Louis, Mo.).

One concern about using cationic polymers as therapeutic agents is their potential toxicity since certain cationic carriers are know to have high cytotoxicity (Hunter, Adv. Drug Deliv. Rev. 58:1523-1531 (2006)). Poly L-lysine (10 -40

µg/ml) has been shown to induce significant apoptosis of mammalian cells (Symonds et al, FEBS Lett. 579:6191-6198 (2005)). By contrast, the $LD_{50}$ of CDP is 200 mg/kg in mice (Hwang et al, Bioconjug. Chem. 12:280-290 (2001)). Therefore, the cytotoxicity of the cationic polymers used in the current study was evaluated on macrophages (FIG. 6). Poly L-lysine and PPA-DPA induced over 50% cell death at approximately 20 and 40 µg/ml, respectively, while PAMAM, protamine and HDMBr induced over 50% cell death at about 160, 280 and 600 µg/ml, respectively. The CDP polymer was well tolerated on macrophages. In mice injected with the CDP, HDMBr and PAMAM at 40 mg/kg, no adverse effects on viability were observed (data not shown). In summary, poly L-lysine and PPA-DPA have a relatively high cytotoxicity while PAMAM, HDMBr and CDP have much less toxicity in vitro and in vivo.

Figure 4:
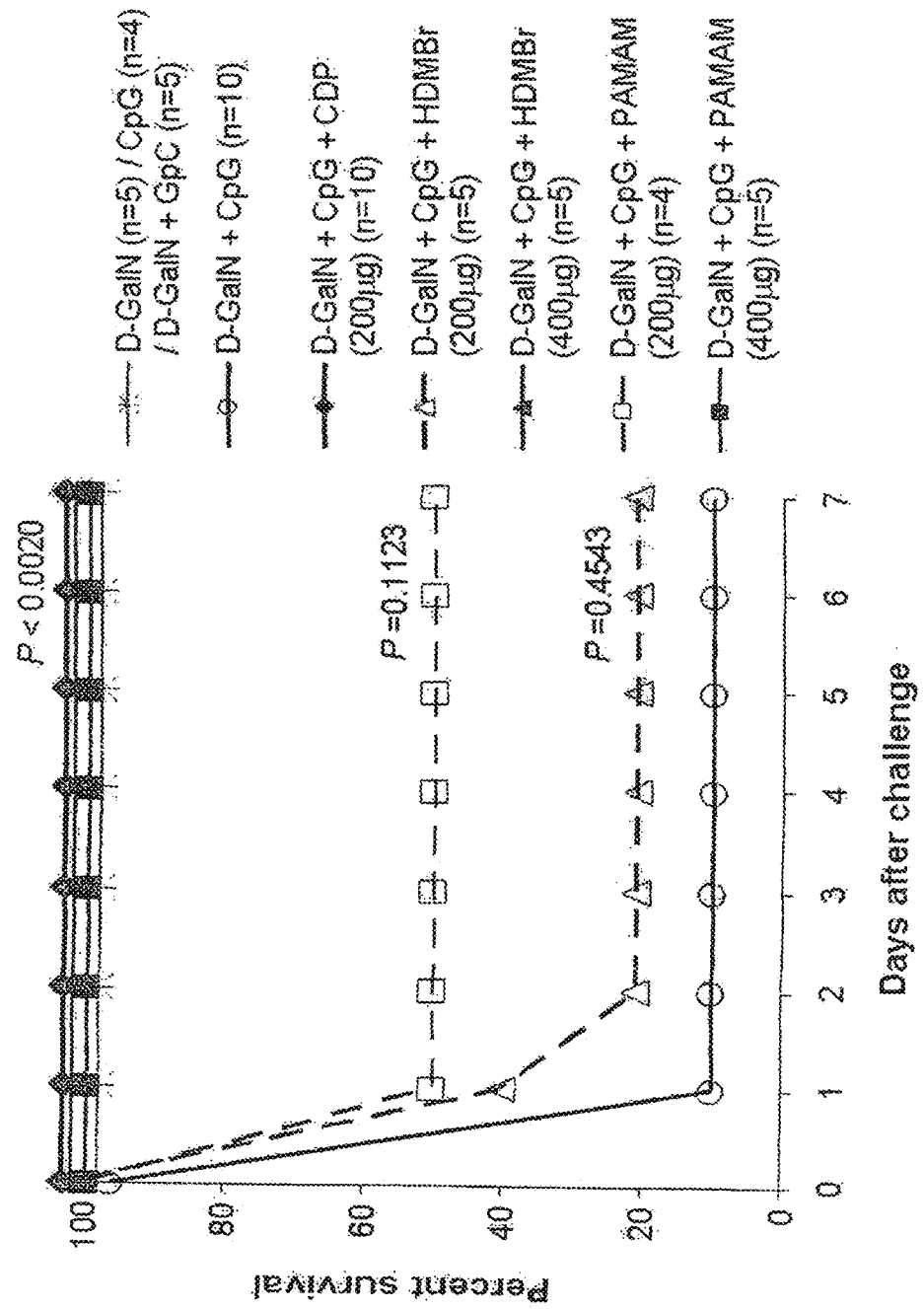
FIGS. 4A-4C. TLR3-or TLR9-mediated acute liver inflammation can be alleviated by nucleic acid-binding polymers.

Finally, the ability of the nucleic acid-binding polymers to limit endosomal TLR activation in vivo was evaluated. It has been shown that injection of CpG DNA or poly I:C into mice sensitized with D-galactosamine (D-GalN) induces a TLR-mediated acute inflammatory response which can result in liver damage and death (Alexopoulou et al, Nature 413:732-738 (2001), Duramad et al, J. Immunol. 174:5193-5200 (2005)). Consistent with previous reports, greater than 90% of the mice died by 48 hours following administration of D-GalN and CpG DNA or poly I:C while none of the mice injected with D-GalN alone, CpG DNA alone or D-GalN and control GpC DNA died. Strikingly, administration of one of three different nucleic acid-binding polymers, CDP, HDMBr or PAMAM, immediately following D-GalN and CpG DNA or poly I:C resulted in significant protection of the animals in a dose-dependent manner and reduced mortality by almost 100% in several cases (FIGS. 4A and 4B). Histological examination of livers from treated mice also demonstrated that inflammation and associated hemorrhage were greatly reduced in the polymer treated animals (FIG. 4C).

Figure 7:
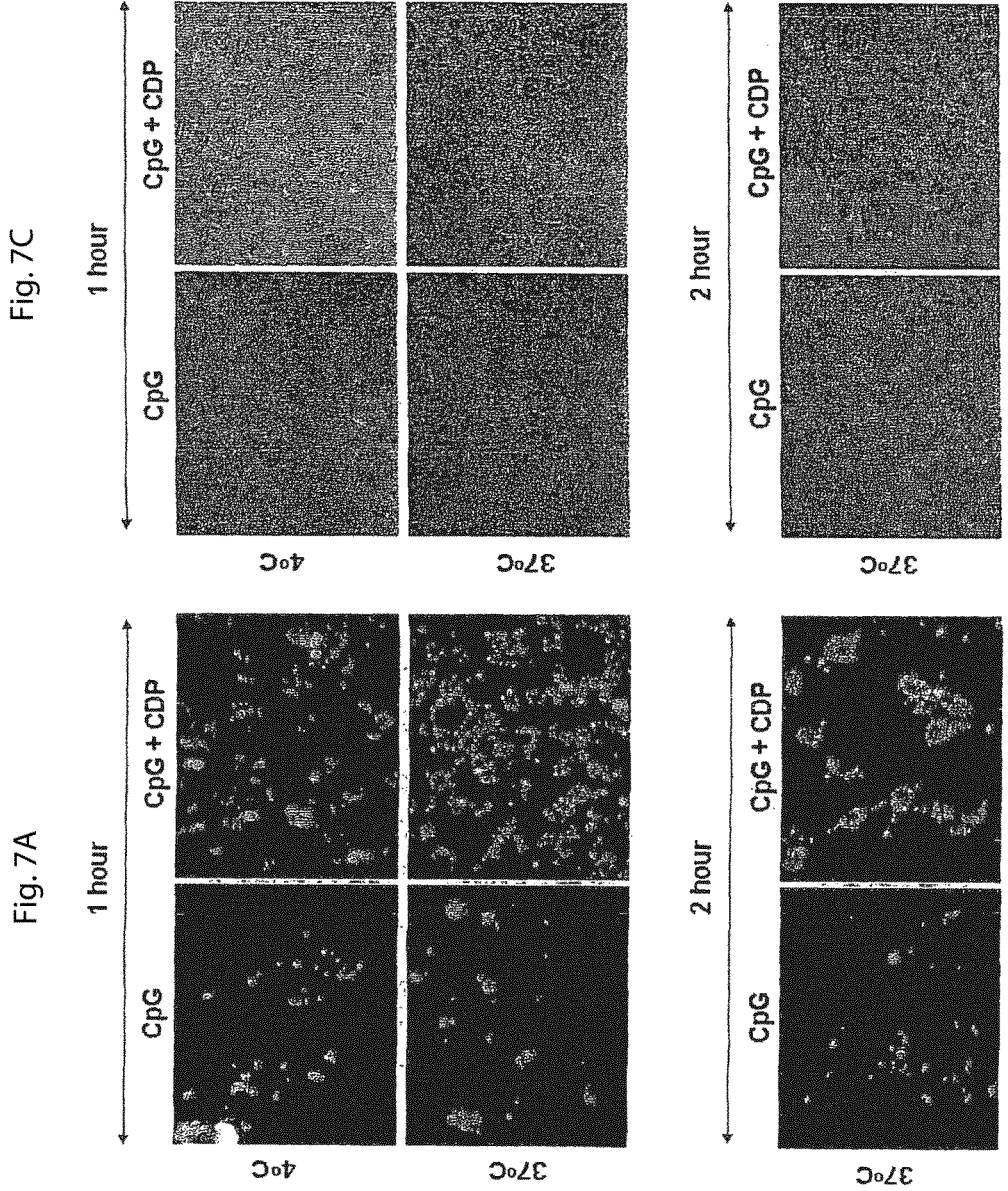
FIGS. 7A-7D. CDP enhanced CpG uptake of cells. Raw264.7 cells ($1\times10^5$ cells/well) were cultured overnight in 8-well chamber slide (Nalge Nunc International Corp, Naperville, Ill.). After thrice washing with cold complete media, cells were replenished with fresh complete media including 1 µM of CpG conjugated with 6-FAM at 5' end with or without 10 µg/ml of CDP. Cells were incubated for 1 (FIGS. 7A and 7C) or 2 hours (FIGS. 7B and 7D) at either 4° C. or 37° C. Fluoresce signals were observed with the Olympus IX71 Inverted Microscope (Olympus, Center Valley, Pa.). The images were analyzed using the Olympus DP Controller Ver.1.2.1.108. Data represents two individual experiments. Magnification is 40×.

Cationic polymers are commonly used for gene or siRNA delivery and are designed to facilitate cellular internalization and endosomal escape (Morille et al, Biomaterials 29:3477-3496 (2008)). Because they traffic through the endosomal compartment, cationic lipids have been used to deliver siRNAs and immune stimulatory ssRNAs to activate endosomal TLR7 or TLR8 (Judge et al, Nat. Biotechnol. 23:457-462 (2005), Sioud, J. Mol. Biol. 348:1079-1090 (2005)). Moreover, synthetic ssRNAs or mRNAs pre-condensed with protamine induced inflammatory cytokine production in human PBMCs via activation of TLR7 or TLR8 (Scheel et al, Eur. J. Immunol. 35:1557-1566 (2005)). Similarly, it was observed that treatment with protamine did not block but significantly enhanced inflammatory cytokine production from cells stimulated with poly I:C (FIG. 1A). In striking contrast, it was observed in the above-described studies that the cationic polymers, CDP, HDMBr and PAMAM, neutralize the ability of nucleic acid-based TLR3 and TLR9 ligands to activate their cognate TLRs and induce inflammatory responses. Several potential explanations exist for these observed differences. In the present studies, cells were treated with endosomal TLR ligands and cationic polymers separately while in the previous studies immune stimulatory RNAs were pre-condensed with cationic molecules before exposure to cells. Thus, the pre-condensation of RNA and cationic molecules could generate a particle that might be efficiently endocytosed. By contrast, nucleic acids, that are not assembled into particles, may be only poorly taken up by cells and addition of the polymers would form small complexes not recognized by the cell. To test this possibility, the cellular uptake of CpG DNAs was evaluated. Unexpectedly, treatment with CDP enhanced cellular uptake of CpG DNAs, even though this did not lead to endosomal TLR9 activation (FIG. 7). The reason why CpG delivered into cells in this manner does not elicit a TLR response is unclear. The polymer may alter endosomal maturation and thus TLR signaling or the polymer may directs the CpG into a distinct intracellular trafficking pathway (Morille et al, biomaterials 29:3477-3496 (2008), Krieg, Annu. Rev. Immunol. 20:709-760 (2002), Jozefowski et al, J. Leukoc. Biol. 80:870-879 (2006)). Further investigation will be required to understand how cationic polymers neutralize nucleic acid activation of endosomal TLRs and why some cationic polymers are more effective than others at impeding such responses.

In summary, nucleic acid-binding polymers can simultaneously limit the activation of multiple endosomal TLRs. As such, these polymers represent promising therapeutic agents for treating patients with inflammatory diseases and autoimmune diseases. Additional preclinical and clinical studies will evaluate this possibility.

All documents and other information sources cited above are hereby incorporated in their entirety by reference.

What is claimed is:

1. A method of treating systemic lupus erytheatosis in a patient comprising administering to the patient a therapeutically effective amount of an agent that binds a nucleic acid, wherein the agent comprises a positively charged PAMAM and wherein the agent binds the nucleic acid such that nucleic acid-induced activation of a toll-like receptor (TLR) is inhibited.

2. The method of claim 1, wherein the agent is orally, transdermally, intravenously, intramuscularly, intraperitoneally, or subcutaneously administered.

3. The method of claim 2, wherein the agent is administered by injection.

4. The method of claim 1, wherein the patient is administered a pharmaceutical composition comprising the therapeutically effective amount of the agent and a carrier, a diluent, or an excipient.

5. The method of claim 1, wherein the agent binds the nucleic acid in a manner that is independent of nucleotide sequence, chemistry or structure.

* * * * *